United States Patent [19]

Garber et al.

[11] 4,070,372
[45] Jan. 24, 1978

[54] PROCESS FOR THE PREPARATION OF THE 2-DIETHOXYPHOSPHINYLIMINO-1,3-DITHIETANE

[75] Inventors: Murray Garber, Lawrenceville; David William Reger, Trenton, both of N.J.

[73] Assignee: American Cyanamid Company, Stamford, Conn.

[21] Appl. No.: 695,692

[22] Filed: June 14, 1976

[51] Int. Cl.$^2$ .......................................... C07D 339/00
[52] U.S. Cl. ............................................... 260/327 M
[58] Field of Search ................................... 260/327 M

[56] References Cited

U.S. PATENT DOCUMENTS 3,470,207  9/1969  Addor .................................. 260/327

OTHER PUBLICATIONS

Houben-Weyl, Methoden der Organischen Chemie, vol. 12/2, pp. 587–588, 795–796.

Primary Examiner—Cecilia M. S. Jaisle
Attorney, Agent, or Firm—Harry H. Kline

[57] ABSTRACT

There is provided a fully integrated process for preparing a 2-dialkoxyphosphinylimino-1,3-dithietane in good overall yields with considerable savings in materials, time and labor involving a plurality of steps comprising the overall reaction of a dialkoxyphosphoryl chloride and an alkali metal or ammonium thiocyanate to obtain a dialkoxyphosphinyl isothiocyanate, reacting the latter with 1.1 to 1.2 molar equivalents of an alkali mercaptan in the presence of a water:acetone mixture (1:9 to 1:3), and finally reacting resultant dialkoxyphosphinyldithiocarbamate with methylene bromide or methylene iodide to obtain a 2-dialkoxyphosphylimino-1,3-dithietane.

5 Claims, No Drawings

PROCESS FOR THE PREPARATION OF THE 2-DIETHOXYPHOSPHINYLIMINO-1,3-DITHIETANE

The broad spectrum contact and systemic pesticide, 2-diethoxyphosphinylimino-1,3-dithietane, represented by the formula (I) below:

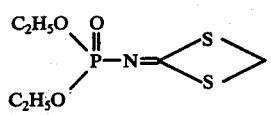

and a method of preparation thereof have been disclosed in U.S. Pat. No. 3,470,207, issued on Sept. 30, 1969, and U.S. Pat. No. 3,553,319, issued on Jan. 5, 1971. The intermediate product, diethoxyphosphinyldithiocarbamate, and a method for the preparation thereof have been disclosed in U.S. Pat No. 3,476,837, issued on Nov. 4, 1969. Each of the above referred-to patents is incorporated herein by way of reference.

The aforementioned pesticide has been found to be effective for the control of soil dewlling nematodes and, especially, for the control of root-knot nematodes (*Meloidogyne incognita*). Thus, it is of cconsiderable interest and importance to be able to manufacture 2-diethoxyphosphinylimino-1,3-diethietane economically on a large scale.

Unfortunately, the preparation of 2-diethoxyphosphinylimino-1,3-dithietane, while satisfactory for small scale laboratory preparations by methods known in the art, is not entirely suitable for large scale preparation of said compound. For comparative and illustrative purposes, one such prior art process consisting of three distinct and separate steps is hereinbelow briefly described and graphically illustrated:

Step 1

One molar equivalent of diethoxyphosphoryl chloride of formula (II) is reacted with a 1.1 to 1.2 molar equivalent of dry ammonium thiocyanate in the presence of an inert solvent, such as benzene, toluene, xylene or the like, at about 20° C to 30° C. The thus-obtained solution of diethoxyphosphinyl isothiocyanate of formula (III) is washed several times with water and dilute sodium bicarbonate solution, and then the isothiocyanate is isolated by removing the solvent in vacuo. This reaction step may be graphically illustrated as follows:

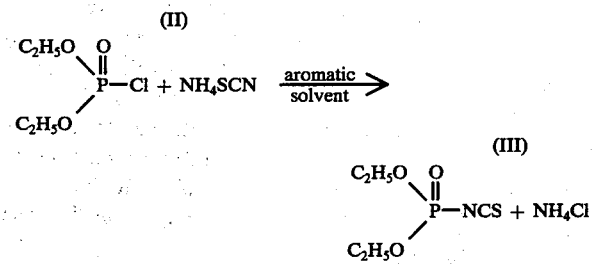

Step 2

The isothiocyanate of formula (III) obtained in Step 1 above, is reacted with a 1.1 to 1.2 molar equivalent of alkali metal mercaptan, such as sodium or potassium hydrosulfide, freshly prepared in situ, prior to the addition of said isothiocyanate, from hydrogen sulfide and sodium or potassium hydroxide or alkoxide (e.g. *t*-butoxide) in a lower ($C_1$-$C_3$) alcohol, to yield the corresponding diethoxyphosphinyldithiocarbamate of formula (IV). This reaction is quite rapid and is complete in a relatively short time. The thus-obtained dithiocarbamate of formula (IV) may be isolated if desired, but the isolation procedure is cumbersome, and since the dithiocarbamate is relatively unstable, it is more advantageous to use the as is reaction mixture in the following final step. This reaction step may be graphically illustrated as follows:

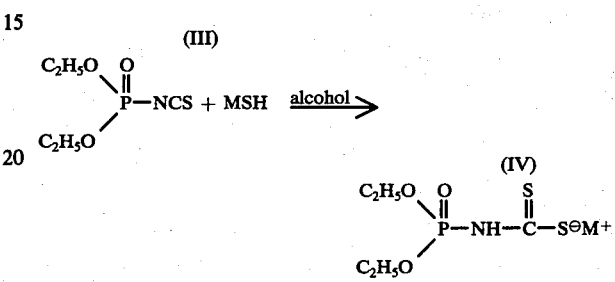

where M is sodium or potassium.

Step 3

To the above reaction mixture 2.5 to 10 molar equivalents of methylene bromide or methylene iodide, are added in the presence of an acid acceptor, such as sodium bicarbonate. The reaction mixture is then stirred at room temperature for from 20 to 24 hours to yield 2-diethoxyphosphinylimino-1,3-dithietane of formula (I). The product dithietane is isolated from the reaction mixture by standard laboratory procedures and purified, if necessary. This reaction step may be graphically illustrated as follows:

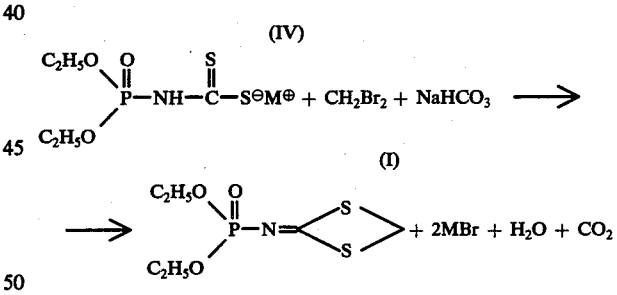

where M is sodium or potassium.

As hereinabove stated, this and similar processes of the art, while suitable for small scale preparations of 2-diethoxyphosphinylimino-1,3dithietane, are not suitable for large scale manufacturing processes. The use of solvents, the relatively long reaction times required, and the need for the purification of the intermediates coupled with the inevitable losses suffered during the work-up and purification of the intermediates and of the end product make this and similar approaches economically undesirable.

Surprisingly, it has been found that the desired 2-diethoxyphosphinylimino-1,3-dithietane of formula (I) may be conveniently prepared in excellent overall yields by the novel fully integrated process of the present invention. The term "fully integrated process" is employed to indicate that in this process the hereinabove described individual reaction steps leading to the desired formula (I) dithietane are combined into one continuous and interlocking sequence of reactions, whereby either the need to isolate or purify the intermediates in both is eliminated. Rather, the as-is reaction mixtures containing intermediates and any by-products and impurities formed in the reaction, are used in each subsequent step of the process. Additionally, the reaction times for each step are shortened without adverse affect on yields; and the product: 2-diethoxyphosphinylimino-1,3-dithietane is obtained in excellent overall yields.

The fully integrated process of the present invention is hereinbelow described and graphically illustrated in detail:

STEP 1

One molar equivalent of diethoxyphosphoryl chloride of formula (II) above is reacted neat with a 1.0 to 1.2 molar equivalent of sodium, potassium or ammonium thiocyanate at a temperature range of 5° C to 30° C and, preferably, 15° C to 25° C for a period of time from 2 to 4 hours to yield diethoxyphosphinyl isothiocyanate of formula (III), above. The reaction is slightly exothermic, easily controlled by a cooling bath.

The as-is reaction mixture containing the isothiocyanate of formula (III) is used without delay in the following step.

STEP 2

The reaction mixture of Step 1 containing the isothiocyanate of formula (III) is added slowly to a water:acetone mixture containing 1.1 to 1.2 molar equivalents of sodium or potassium hydrosulfide wherein the ratio of water:acetone is established in the range of 1:9 to 1:3 and, preferably, in the ratio of 1:3, at a temperature ranging from 5° C to 25° C. The reaction is exothermic. It is controlled by means of a suitable cooling bath. The reaction is rapid and is complete in about 10 to 15 minutes after the addition of the Step 1 reaction mixture is completed. The reaction mixture of Step 2 containing diethoxyphosphinyldithiocarbamate is utilized in the final step of the process.

Step 3

One to 2.0 molar equivalent of a methylene halide such as methylene bromide, or methylene iodide, and one to two molar equivalents of sodium bicarbonate are added to the Step 2 reaction mixture. Resultant slurry is stirred at about 20° C to 30° C and, preferably, at 25° C for from about 4 to 8 hours and, preferably, for 6 hours. Acetone is next stripped from the reaction mixture and the product extracted with an aromatic solvent such as toluene. The thus-obtained solution of 2-diethoxyphosphinylimino-1,3-dithietane is washed with water and dilute sodium bicarbonate solution and the product is isolated, if desired, by removing the aromatic solvent in vacuo.

The preferred embodiment of the above-described fully integrated process may be graphically illustrated as follows:

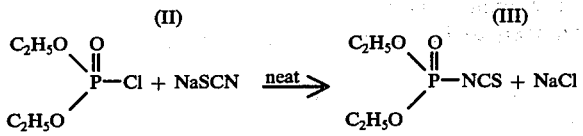

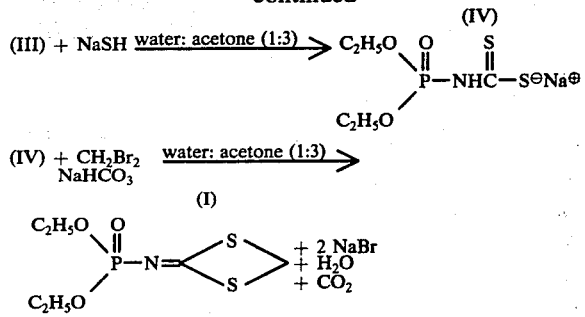

By the above fully integrated process formula (I) product is obtained in 60% to 68% overall yields.

It has been unexpectedly found that the methylene halide reactant of Step 3 may be introduced in Step 1 of the above described fully integrated process. This seemingly minor change in the overall process is quite significant and of marked advantage on a large scale. First, the above-identified thiocyanates are hygroscopic and thus tend to absorb moisture from the air while being added to the diethoxyphosphoryl chloride and thus normally would require protective blanketing with an inert dry gas, such as nitrogen, and special equipment to load the reactor, since the presence of even small amounts of water significantly reduce the yields of this reaction step. The use of the above-identified methylene halide reactant of Step 3 as an inert diluent and reaction medium in Step 1 allows for the rapid introduction of the thiocyanate into the reactor with minimum exposure to air and the moisture contained therein and, thereafter, said methylene halide serves as a protective liquid blanket preventing said thiocyanate from absorbing moisture from the air. This eliminates the need for the use of special equipment as well as an inert gas during the addition of said thiocyanate.

Advantageously, the aforementioned change allows for the addition of liquid diethoxyphosphoryl chloride in a closed system to the stirred thiocyanate-methylene halide mixture. Since the resultant reaction is exothermic, the exotherm is easily controlled by adjusting the rate of addition of the phosphoryl chloride. Additionally, as an inert diluent, the methylene halide allows for a more thorough stirring, mixing and pumping of an otherwise thick reaction mixture. Thus, there is not any need to employ special high powered stirring and pumping equipment and, therefore, additional savings in energy requirements can be realized. Clearly, the methylene halide is present in Step 2. However, in Step 3 it becomes a reactant and such modification does not affect the overall yield.

It has further been found that where the hereinabove defined water:acetone ratios are not used, the yields of formula (I) product are significantly reduced.

Substitution of bromochloromethane or methylene chloride for methylene bromide (or iodide) in the above fully integrated process also results in significantly reduced yields of 2-diethoxyphosphinylimino-1,3-dithietane and is not preferred herein.

In general, analogs of formula (I), namely, 2-diethoxyphosphinylimino-1,3-dithietane, represented by formula:

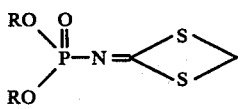

wherein R is selected from the group consisting of methyl, propyl, isopropyl and butyl, are contemplated. These can be prepared by the novel fully integrated process of the present invention.

The desired 2-diethoxyphosphinylimino-1,3-dithietane having nematocidal properties may be formulated as liquid or emulsifiable concentrates, wettable powders, dusts, dust concentrates and granular formulations according to the needs and demands of the users thereof.

The following non-limiting examples are incorporated herein to further illustrate the present invention.

EXAMPLE 1

Preparation of
2-Diethoxyphosphinylimino-1,3-dithietane

Ammonium thiocyanate (67.0 g; 0.88 mole) is added at 5° to diethoxyphosphoryl chloride (138.0 g; 0.80 mole). The resulting thick slurry is stirred at 25° C for 4 hours, then is cooled to 5° C and treated with chilled water (175 ml). A two phase system forms and is stirred for 3 minutes and then the bottom organic phase consisting of diethoxyphosphinyl isothiocyanate is separated.

The diethoxyphosphinyl isothiocyanate obtained in the above step is then added dropwise at 10° C to a solution of sodium hydrosulfide monohydrate (74.0 g – 73% real; 1.0 mole) in water (96 ml) and acetone (328 ml) while maintaining the reaction temperature below 25° C in an ice bath. Ten minutes after the addition is completed, sodium bicarbonate (134.4 g; 1.6 mole) and methylene bromide (139.1 g; 0.80 mole) are added to the reaction mixture and the resulting slurry is stirred at 25° C for 16 hours.

The acetone is then stripped from the reaction mixture and toluene (400 ml) added to the residue. The toluene slurry is stirred with water (240 ml) to dissolve most of the solids. The two phase reaction mixture is then filtered and the aqueous phase separated. The toluene phase is washed with saturated aqueous sodium bicarbonate solution (240 ml) and is then evaporated to constant weight under vacuum to yield 142.0 g (86.5% real, 63.9% yield) of 2-diethoxyphosphinylimino-1,3-dithietane.

The above process is repeated, except that the diethoxyphosphinyl isothiocyanate obtained in the first step is not isolated. Rather, the as-is reaction mixture containing the isothiocyanate is used immediately in the next step of the process and in the third step, the reaction is terminated in 6 hours.

Substitution of dimethoxyphosphoryl chloride, diisopropoxyphosphoryl chloride or di-n-butoxyphosphoryl chloride for diethoxyphosphoryl chloride in the above example yields 2-dimethoxyphosphinylimino-1,3-dithietane, 2-diisopropoxyphosphinylimino-1,3-dithietane or 2-di-n-butoxyphosphinylimino-1,3-dithietane, respectively.

EXAMPLE 2

Preparation of
2-Diethoxyphosphinylimino-1,3-dithietane

Diethoxyphosphoryl chloride (138.0 g; 0.80 mole) is added at 5° C to a stirred mixture of dry ammonium thiocyanate (67.0 g; 0.88 mole) and methylene bromide (139.1 g; 0.80 mole), and the resulting reaction mixture is stirred at 25° C for 4 hours.

The above reaction mixture, containing the intermediate diethoxyphosphinyl isothiocyanate, is then added slowly at 10° C to a solution of sodium hydrosulfide monohydrate (74.0 g – 73% real; 1.0 mole) in water (96 ml) and acetone (328 ml) while maintaining the reaction temperature below 25° C in an ice bath. Ten minutes after the addition is completed, sodium bicarbonate (134.4 g; 1.6 mole) is added to the reaction mixture and the resulting slurry is stirred at 25° C for 6 hours.

The acetone is then stripped from the reaction mixture and toluene (400 ml) added to the residue. The toluene slurry is stirred with water (240 ml) to dissolve most of the solids. The two phase reaction mixture is then filtered and the aqueous phase separated. The toluene phase is washed with saturated aqueous sodium bicarbonate solution (240 ml) and is then evaporated to constant weight under vacuum to yield 2-diethoxyphosphinylimino-1,3-dithietane.

EXAMPLE 3

This example illustrates the effect of water:acetone ratios on the yield of 2-diethoxyphosphinylimino-1,3-dithietane.

The process of Example 1 is repeated except that in Steps 2 and 3 the water:acetone ratios are varied. The water:acetone ratios and yields are summarized in Table I below:

Table I

| Parts by Volume Water:acetone Ratios | Percent Yield of Theory |
|---|---|
| 0 (No acetone) | 49.4 |
| 50:1 | 53.1 |
| 10:1 | 59.2 |

It can be seen from Table I that the overall yields of the process decrease as the volume of water in the water:acetone mixture is increased beyond the 1:3 to 1:9 range.

EXAMPLE 4

This example illustrates the effect of water:acetone ratios on the yield of 2-diethoxyphosphinylimino-1,3-dithietane when utilizing Step 3 reaction of the process of the present invention.

A mixture of methylene bromide (8.7 g; 0.05 mole), sodium bicarbonate, acetone and water is stirred rapidly at 10° C and potassium diethoxyphosphinyldithiocarbamate added over 10 minutes. The temperature of the reaction mixture is adjusted to 25° and the reaction is allowed to stir for 25 hours.

The acetone is then stripped from the reaction mixture and toluene (25 ml) added to the residue. The two phase reaction mixture is separated. The toluene phase is washed with saturated aqueous sodium chloride (50 ml), then with saturated aqueous sodium bicarbonate (50 ml) and saturated aqueous sodium chloride (50 ml). The toluene phase is then evaporated to constant weight under vacuum to afford 2-diethoxyphosphinylimino-1,3-dithietane. The water:acetone ratios and the yields are summarized in Table II below:

Table II

| Parts by Volume Water:acetone Ratio | Percent Yield of Theory |
|---|---|
| 1:20 | 64.8 |
| 1:40 | 63.36 |
| 1:7 | 74.34 |
| 1:3 | 72.18 |

It can be seen from Table II that the yields in Step 3 of the process decreases as the volume of the acetone in the water:acetone mixture is increased beyond the 1:3 to 1:9 range.

EXAMPLE 5

Evaluation of 2-Diethoxyphosphinylimino-1,3-dithietane for the control of root-knot nematode (*Meloidogyne incognita*) on tomato in the greenhouse A. Material
2-Diethoxyphosphinylimino-1,3-dithietane.
B. Plant
Tomato (*Lycopersicon esculentum;* cv. Bonny Best).
C. Infective Agent
Root-knot Nematode (*Meloidogyne incognita*) inoculum.

Application Rates/Liter of Potting Soil
(Equivalent to Pound/Acre - Broadcast)

2-Diethoxyphosphinylimino-1,3-dithietane at 0.75 mg, 1.5 mg and 3.0 mg/liter of soil.

Procedure

Acetone solutions of the sample are prepared at the appropriate concentrations. One liter of moist potting soil is placed in a suitable stainless steel beaker. One ml of candidate solution is distributed, drop by drop, over the surface of the soil. The beaker is then capped and placed on an off-center rotary mixer and mixed for 2 minutes (about 60 revolutions). After mixing, the soil is divided between two 0.5 liter paper cups by filling the cups half full of soil then distributing 25 ml root-knot nematode inoculum on the soil and filling the remainder of the container with treated soil. Seedling tomato plants are transplanted into the cups of soil the same day, watered and removed to the greenhouse. After about 4 weeks, the tomato plants are carefully removed from the containers, the soil washed away from the roots, and the roots are then examined for nematode galling.

The roots are indexed for galling by the following system:
0 = No visible galling.
T = Less than 1% of roots with galls.
1 = 1–5% of roots galled.
2 = 6–10% of roots galled.
3 = 11–20% of roots galled.
4 = 21–30% of roots galled.
5 = 31–40% of roots galled.
6 = 41–50% of roots galled.
7 = 51–60% of roots galled.
8 = 61–70% of roots galled.
9 = 71–80% of roots galled.
10 = 81–100% of roots galled.

The results obtained are summarized in Table III below.

Table III

Evaluation of 2-Diethoxyphosphinylimino-1,3-dithietane for the Control of Root-knot Nematode (*Meloidogyne incognita*) on Tomato in the Greenhouse

| Compound | Rate mg/l | Root-knot Index | | | Average of 3 Replicates |
|---|---|---|---|---|---|
| | | 1 | 2 | 3 | |
| 2-Diethoxyphosphinylimino-1,3-dithietane | 0.75 | 8 | 8 | 5 | 7.0 |
| | 1.5 | 6 | 6 | 2 | 4.7 |
| | 3.0 | 0 | 0 | T | 0–T |
| Infected Controls | — | 10 | 10 | 10 | 10.0 |
| Non-infected Controls | — | 0 | 0 | 0 | 0.0 |

We claim:
1. A fully integrated process for the preparation of a compound of formula:

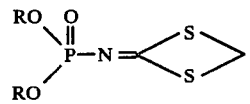

wherein R is $C_1$–$C_4$ alkyl; consisting essentially in the steps of: reacting one molar equivalent of a compound of the formula:

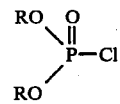

wherein R is as above defined, with a 1.0 to 1.2 molar equivalent of a thiocyanate selected from the group consisting of sodium-, potassium- and ammonium thiocyanate at a temperature range of 5° C to 30° C for a period of time so as to obtain a compound of formula:

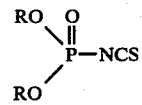

wherein R is as above defined; reacting the thus-formed compound without isolation from the above-said reaction mixture and in the presence of same with a 1.1 to 1.2 molar equivalent of sodium or potassium hydrosulfide in a water:acetone solvent system wherein the ratio of water:acetone is established in the range of 1:3 to 1:9 at a temperature range of 5° C to 30° C for a period of time so as to obtain a compound of the formula:

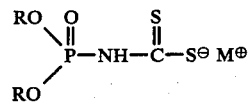

wherein R is as above defined and M is an alkali metal, and reacting (*a*) the thus-formed compound in said water:acetone solvent system and in the presence of the reaction media with (*b*) a one to 2 molar equivalent of a methylene halide selected from the group consisting of methylene bromide and methylene iodide in the presence of a 1 to 2 molar equivalent of an alkali metal bicarbonate at a temperature of 25° C to 35° C for a period of time sufficient to essentially complete the reaction.

2. The fully integrated process according to claim 1, wherein R is ethyl; the thiocyanate is ammonium thiocyanate and the reaction temperature is 25° C; the hydrosulfide is sodium hydrosulfide, the ratio of water:acetone in the solvent system is 1:3, and the reaction temperature is 25° C; the methylene halide is methylene bromide, and the reaction temperature is 25° C.

3. The fully integrated process according to claim 2, wherein the thiocyanate is sodium thiocyanate.

4. The fully integrated process for the preparation of a compound of formula:

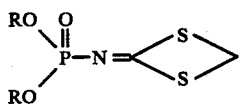

wherein R is $C_1$-$C_4$ alkyl; consisting essentially in reacting one molar equivalent of a compound of formula:

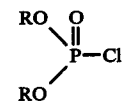

wherein R is as above defined, with a 1.0 to 1.2 molar equivalent of a thiocyanate selected from the group consisting of sodium-, potassium- and ammonium thiocyanate in the presence of one molar equivalent of a methylene halide selected from the group consisting of methylene bromide and methylene iodide at a temperature range of 5° C to 30° C for a period of time sufficient to essentially complete the reaction and obtain a compound of formula:

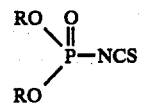

wherein R is as above defined; reacting the thus formed compound without isolation from the above-said reaction mixture, in the presence of said reaction medium and the methylene halide added, with a 1.1 to 1.2 molar equivalent of sodium or potassium hydrosulfide in a water:acetone solvent system wherein the ratio of water:acetone is established and maintained in the range of 1:3 to 1:9 at a temperature range of 5° C to 30° C for a period of time sufficient to essentially complete the reaction and obtain a compound of the formula:

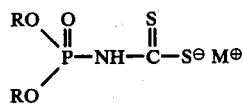

wherein R is as above defined and M is an alkali metal, and reacting the compound thus formed without isolation in said water:acetone solvent system, and in the presence of the reaction media, with the above-defined 1 to 2 molar equivalent of methylene halide present in the reaction mixture from the start of said fully integrated process, in the presence of a 1 to 2 molar equivalent of sodium bicarbonate at a temperature range of 25° C to 35° C for a period of time sufficient to essentially complete the reaction.

5. The fully integrated process according to claim 4, wherein R is ethyl, the methylene halide is methylene bromide the thiocyanate is sodium thiocyanate; the hydrosulfide is sodium hydrosulfide, the ratio of water:acetone in the solvent system is 1:3; and maintaining the reaction temperature at 25° C.

* * * * *